US012667737B2

(12) United States Patent
Hofmann et al.

(10) Patent No.: US 12,667,737 B2
(45) Date of Patent: Jun. 30, 2026

(54) METHOD FOR PROVIDING AN IRRADIATION PLAN, DEVICE FOR DETERMINING AND DEVICE FOR APPLYING THE IRRADIATION PLAN

(71) Applicant: SIEMENS HEALTHINEERS AG, Forchheim (DE)

(72) Inventors: Christian Hofmann, Erlangen (DE); Patrick Wohlfahrt, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 165 days.

(21) Appl. No.: 18/303,742

(22) Filed: Apr. 20, 2023

(65) Prior Publication Data

US 2023/0338749 A1 Oct. 26, 2023

(30) Foreign Application Priority Data

Apr. 21, 2022 (DE) ..................... 10 2022 203 903.3

(51) Int. Cl.
*A61B 5/00* (2006.01)
*A61N 5/10* (2006.01)
(52) U.S. Cl.
CPC ......... *A61N 5/1039* (2013.01); *A61N 5/1037* (2013.01); *A61N 5/1049* (2013.01)
(58) Field of Classification Search
CPC .. A61N 5/1039; A61N 5/1037; A61N 5/1049; A61N 5/1067; A61N 5/1068;
(Continued)

(56) References Cited

U.S. PATENT DOCUMENTS

2009/0180589 A1 7/2009 Wang et al.
2010/0023094 A1 1/2010 Smith et al.
(Continued)

FOREIGN PATENT DOCUMENTS

CN 109199423 A * 1/2019 .......... A61B 5/0803
DE 102020211944 A1 3/2022
(Continued)

OTHER PUBLICATIONS

Translation of CN109199423A (Year: 2019).*
(Continued)

*Primary Examiner* — Uzma Alam
*Assistant Examiner* — Mamadou Faye
(74) *Attorney, Agent, or Firm* — Harness, Dickey & Pierce, P.L.C.

(57) ABSTRACT

A method for providing an irradiation plan for irradiation of a target volume, comprises: acquiring a time-resolved 3D image dataset, wherein the 3D image dataset is time-resolved over at least one respiratory cycle of the patient, wherein the 3D image dataset is based on a time-resolved scan of an examination region of the patient and on an imaging respiration profile, wherein the examination region includes the target volume, and wherein the imaging respiration profile is based on a first respiration-correlated surrogate variable determined during the time-resolved scan; acquiring a respiration-correlated second surrogate variable of the patient, wherein the second surrogate variable describes a respiration of the patient during the irradiation; determining an irradiation respiration profile based on the second surrogate variable; determining the irradiation plan based on the 3D image dataset and the irradiation respiration profile; and providing the irradiation plan for an irradiation of the target volume.

20 Claims, 4 Drawing Sheets

(58) Field of Classification Search

CPC .......... A61N 5/1001; A61N 2005/1052; A61N 2005/1055; A61N 2005/1059; A61N 2005/1061; A61B 5/0036; A61B 5/087; A61B 5/4848; A61B 5/7267; A61B 5/0073; A61B 5/1135; A61B 6/5288; A61B 5/055; A61B 6/032; A61B 6/037; G01T 1/2985

See application file for complete search history.

(56) References Cited

U.S. PATENT DOCUMENTS

| | | | | |
|---|---|---|---|---|
| 2013/0035588 A1* | 2/2013 | Shea | ................ | G01R 33/56308 |
| | | | | 600/413 |
| 2017/0095197 A1* | 4/2017 | Kleiner | ................. | A61B 6/486 |
| 2017/0312544 A1 | 11/2017 | Mori et al. | | |
| 2017/0367612 A1* | 12/2017 | Kawrykow | ...... | G01R 33/56325 |
| 2020/0179722 A1* | 6/2020 | Packer | ................ | A61N 5/1037 |
| 2021/0187321 A1 | 6/2021 | Maguire et al. | | |
| 2022/0087630 A1 | 3/2022 | Hofmann | | |
| 2023/0157650 A1 | 5/2023 | Hofmann et al. | | |

FOREIGN PATENT DOCUMENTS

| | | |
|---|---|---|
| EP | 2121097 A2 | 11/2009 |
| EP | 4011294 A1 | 6/2022 |
| WO | WO 2021094824 A1 | 5/2021 |

OTHER PUBLICATIONS

Rietzel et al. Four-dimensional computed tomography: Image formation and clinical protocol, Am. Assoc. Med. Phys. 32 (4), Apr. 2005, p. 874-889. (Year: 2005).*

* cited by examiner

METHOD FOR PROVIDING AN IRRADIATION PLAN, DEVICE FOR DETERMINING AND DEVICE FOR APPLYING THE IRRADIATION PLAN

CROSS-REFERENCE TO RELATED APPLICATION(S)

The present application claims priority under 35 U.S.C. § 119 to German Patent Application No. 10 2022 203 903.3, filed Apr. 21, 2022, the entire contents of which are incorporated herein by reference.

FIELD

One or more example embodiments of the present invention relate to a method for providing an irradiation plan, in particular for the purpose of irradiating a target volume during a radiation therapy of a patient in an irradiation facility. One or more example embodiments of the present invention further relate to a device for providing the irradiation plan and a device, in particular an irradiation facility, for applying the irradiation plan. One or more example embodiments of the present invention also relate to a computer program for applying the method and a storage medium containing the computer program.

BACKGROUND

Computed tomography (CT) images are often used in the course of radiation therapy planning in order to calculate and optimize dose distribution maps and to draw up an irradiation plan. Depending on the location of the tumor, the patient's breathing can have a greater or lesser impact on the irradiation, the irradiation plan and any safety margins. For instance, tumors are known which tend to move due to respiration, e.g. pulmonary or abdominal carcinomas. The movement of a tumor can lead to healthy tissue, in particular vulnerable organs, also being irradiated instead of the actual tumor as the target volume, which it is imperative to avoid, however.

In order to be able to reconstruct an anatomy relevant to the irradiation planning, in particular the pulmonary or abdominal carcinoma, of the patient in a particular respiratory phase of the patient, a respiratory movement of the patient can be captured during the imaging examination, the acquisition of the CT images and a determination of 3D image data. For example, slice images covering all respiratory phases of a respiratory cycle, which in particular maps an inspiration and expiration of the patient and corresponds to a periodic segment of the respiratory movement, can be reconstructed for each z-position of the examination region, in particular of the target volume. This enables time-resolved image datasets or respiration-correlated image series to be generated which visualize the examination region in terms of a respiratory movement in a temporally resolved manner, i.e. substantially at different points in time during the respiratory cycle of the patient. The breathing and respiratory movement of a patient are highly patient-specific. As a result, the same parameters set for the data acquisition via a medical imaging apparatus are not optimal for every patient.

In the prior art, an irradiation plan was determined based on the image data, in particular the time-resolved 3D image data, and drawn up without knowledge and/or consideration of the patient's breathing during an irradiation process. Three-dimensionally reconstructed volumes based on computed tomography scans (4DCT) are used as a time-resolved 3D image dataset, for example. In order to be able to reconstruct the anatomy of a patient in a particular respiratory phase, a surrogate signal is synchronized with the raw data acquisition and consequently a correlation is established between CT raw data and the respiration of the patient. For irradiation planning purposes, the movement of tumors and healthy structures at risk, for example over multiple respiratory phases, is estimated and subsequently, during the irradiation, assumed as movement over the entire respiratory cycle. The movement of the tumor and the healthy at-risk structures determined in this way can then be used for the definition of the target volume that is to be irradiated, e.g. internal target volume (ITV), with additional safety margins on the basis of the different 4DCT phases, a reconstructed mid-ventilation phase or a maximum intensity projection (MIP) dataset.

For a maximum estimation, it is also possible to take into account only the two respiratory phases of maximum inspiration and expiration in each case. The accuracy of this planning is dependent firstly on the image quality of the 4DCT reconstructions, which are often adversely affected by image artifacts. A basic requirement for avoiding these artifacts is that the patient breathes in a regular and reproducible manner (constant respiratory rate and amplitude) during the raw data acquisition for determining the time-resolved 3D data. However, this is not possible for every patient. Consequently, irregularities in the respiratory rate and amplitude lead to inconsistent and incomplete raw data, which leads in turn to image artifacts in the final 4DCT reconstructions. These artifacts represent inaccuracies which have a critical effect on the accuracy of the irradiation planning. To put it simply: The stronger the artifacts, the greater the inaccuracies. The greater the uncertainty in the irradiation planning, the greater are the safety margins that must be taken into account during the irradiation planning.

Imaging methods taking into account the breathing of the patient are known from the publications EP 2121097 and DE 10 2020 211 944 A1. With these, irregularities in patient respiration are taken into account and included during data acquisition and reconstruction. As a result, irregularities in the respiratory rate and amplitude are detected and actively used in order effectively to visualize a "representative" respiratory behavior of the patient in the 4DCT image dataset with significantly fewer image artifacts. These 4DCT images provide a good data foundation for the irradiation planning. Currently, however, irradiation plans are produced and irradiations performed which use the image data exclusively, without taking into account the underlying algorithmics of determining the time-resolved 3D image data, in particular the 4DCT data acquisition. In most cases it can be assumed that the patient also breathes irregularly during the irradiation and consequently deviations from the "ideal" irradiation plan (based on images showing a representative respiration of the patient) occur. This can lead to a situation in which the conformity of the irradiation plan cannot be maintained due to the changes in the anatomy caused by the irregular respiration.

SUMMARY

An object underlying one or more example embodiments of the present invention is to enable an irradiation plan to be determined that is individually tailored to the patient and his or her respiration.

At least this object is achieved by the features of example embodiments and/or the independent claims. Further advantageous embodiments and developments of the present invention, some of which are inventive in their own right, are set forth in the dependent claims, the following description and/or the attached figures.

Within the scope of the example embodiments of the present invention, a method for providing an irradiation plan for an irradiation of a target volume is proposed, the method comprising the steps of:

acquiring a time-resolved 3D image dataset, wherein the 3D image dataset is time-resolved over at least one respiratory cycle of the patient, wherein the 3D image dataset is based on a time-resolved scan of an examination region of a patient and on an imaging respiration profile, wherein the examination region comprises the target volume, wherein the imaging respiration profile is based on a first respiration-correlated surrogate variable determined during the time-resolved scan, acquiring a respiration-correlated second surrogate variable of the patient, wherein the second surrogate variable describes a respiration of the patient during the irradiation, determining an irradiation respiration profile based on the acquired second surrogate variable, determining the irradiation plan based on the time-resolved 3D image dataset and the irradiation respiration profile, providing the irradiation plan for an irradiation of the target volume.

Providing the irradiation plan is understood in particular as a real-time correction of an original irradiation plan, for example a real-time correction based on the patient's breathing and/or in order to take into account the respiration of the patient. The method is embodied in particular for automatic determination of an irradiation plan. For example, the irradiation plan can form a patient-specific irradiation plan, preferably for irradiation by a linear accelerator and/or a particle irradiation facility. The irradiation plan is designed to describe, specify and/or set a time limit for the irradiation of a target volume with ionizing radiation and/or high-energy particles. The irradiation plan is based in particular on a dose distribution that is to be achieved (nominal dose distribution) within said target volume. The irradiation plan serves the purpose of depositing or applying the dose of the (particle) beam with a high degree of quality (e.g. as precisely as possible according to the nominal dose distribution) in the target volume, which preferably comprises multiple isoenergy layers.

In a first method step, a time-resolved 3D image dataset, 3D image dataset or 3D image data for short, is acquired. The 3D image dataset forms in particular a 4DCT image dataset. The 3D image dataset can be provided by a memory, a cloud or a data medium, wherein, as acquisition, may be understood an importing, in particular local storing and/or saving, of the provided 3D image dataset. The 3D image dataset is preferably determined and/or acquired in a method step preceding the first method step. The 3D image dataset can be determined or have been determined for example based on the methods according to the publications EP 2121097 and/or DE 10 2020 211 944 A1, the contents of the publications EP 21210497 and DE 10 2020 211 944 A1 being incorporated herewith.

The 3D image dataset is time-resolved over at least one respiratory cycle of the patient. A respiratory cycle comprises in particular a plurality of respiratory phases. As respiratory phases, the respiratory cycle comprises in particular an inspiration and expiration of the patient. In particular, the respiratory cycle comprises precisely one inspiration and one expiration. There can be differences in the respiratory cycles, in particular the respiratory phases, for a patient, for example in terms of depth, intensity and/or duration of the inspiration and/or expiration. In particular, a pause phase, which can be different for the respiratory cycles, can lie between inspiration and expiration.

The 3D image dataset is based on a scan of an examination region of the patient, in particular a time-resolved scan and/or an acquisition of an image sequence over time. The scan of the examination region is preferably performed using a medical imaging apparatus, preferably using a computed tomography system, a positron-emission tomography system or a magnetic resonance tomography system. As a result of the scanning of the examination region, raw image data can be provided. The raw image data comprises and/or forms slice images, for example. The scan of the examination region is preferably performed over a plurality of respiratory cycles. The scan of the examination region can be performed in an upstream step prior to the proposed method or optionally form a part of the method according to one or more example embodiments of the present invention as a method step preceding the first method step. The examination region comprises the section of the target volume. The target volume is formed for example by the tumor that is to be irradiated. Alternatively and/or in addition, the target volume is given by an organ or is part of an organ. For example, the examination region is a part of the body of the patient in which the target volume is situated.

The time-resolved 3D image dataset is determined based on the scanned examination region, in particular on the raw image data, and an imaging respiration profile. In particular, the time-resolved 3D image dataset is reconstructed based on the imaging respiration profile. For example, the imaging respiration profile comprises and/or describes a respiratory curve of the patient during the scan of the examination region and/or the acquisition of the raw image data. The respiratory curve of the patient, which reflects the respiratory movement of the patient, describes the respiration preferably over a plurality of respiratory cycles, in particular over all the respiratory cycles during the scan of the examination region for determining the 3D image data. The respiratory curve and/or the imaging respiration profile are/is determined based on a first surrogate variable. The first surrogate variable forms a respiration-correlated variable, in particular a measured quantity. For example, the first surrogate variable can be acquired via a sensor, for example via a camera or a respiration belt. The respiratory movement or the imaging respiration profile typically describes a free respiration of the patient and in particular comprises at least one respiratory cycle of the patient. The imaging respiration profile is determined in particular over at least one entire respiratory cycle of the patient, the entire respiratory cycle comprising at least one one-time inspiration and one-time expiration of the patient. The provided respiratory curve and/or the imaging respiration profile preferably comprise/comprises more than one respiratory cycle. The respiratory cycle preferably corresponds to a periodic segment of the respiratory movement. The duration of a respiratory cycle or an average duration of a plurality of succeeding respiratory cycles, and consequently a respiratory rate, i.e. for example a number of inhalations or exhalations per unit time, can be determined from the imaging respiration profile, in particular from the respiratory curve. The slower the patient breathes, the higher is the respiratory rate.

The imaging respiration profile, in particular the variation in the respiratory curve of a patient, may be in particular patient-specific, i.e. occurring gradients, the duration of an inhalation or exhalation, or the occurrence of intermittent rest phases with little or no movement can be different from patient to patient and possibly also from imaging examination to imaging examination of a patient. This can be derivable in particular also independently of an (average) respiratory rate or at least not in a simple manner from an (average) respiratory rate of a patient.

In a further inventive method step, a respiration-correlated second surrogate variable of the patient is acquired, in particular measured. For example, the second surrogate variable is acquired and/or measured via a sensor, for example a respiration belt or a video camera as sensor. The second surrogate variable is or was acquired and/or measured during the irradiation of the patient, for example during the execution of the irradiation plan and/or while the patient is being irradiated. In other words, the first surrogate variable is determined and/or measured during the acquisition of the raw data for the imaging and/or in order to determine the 3D image dataset, whereas the second surrogate variable is determined and/or measured at a later time or during the irradiation of the patient. The second surrogate variable describes the respiration of the patient, for example length, depth and/or gradient of inspiration and expiration phases. For example, the first and/or second surrogate variable describe/describes a rising and falling of a rib cage of the patient.

An irradiation respiration profile is determined, defined and/or calculated based on the determined and/or measured second surrogate variable. For example, the irradiation respiration profile comprises and/or describes a respiratory curve of the patient at the time of and/or during the irradiation and/or the execution of the irradiation plan. In particular, the irradiation respiration profile describes a current respiration and/or forms a real-time irradiation respiration profile. For this purpose, it is provided in particular to acquire and/or measure the second surrogate variable in real time and/or at regular intervals. The respiratory curve optionally included in the irradiation respiration profile describes the respiratory movement of the patient during the irradiation and/or the respiration over a plurality of respiratory cycles.

In a further method step, the method according to one or more example embodiments of the present invention provides the determining of the irradiation plan. The irradiation plan is determined based on the time-resolved 3D image dataset and the irradiation respiration profile. In particular, the irradiation plan can be determined based on a raw irradiation plan or a provisional irradiation plan. The raw irradiation plan is for example an irradiation plan which is embodied and/or suitable for irradiating a patient, in particular a selectable target volume or tumor type. The raw irradiation plan may be embodied as patient-independent, tailored to general boundary conditions such as stature, age and/or physique of the patient. Alternatively, the raw irradiation plan is determined based on the 3D image dataset of the patient, in particular without taking into account the second surrogate variable and/or the irradiation respiration profile. In this case it can be provided that the determining of the irradiation plan is embodied as an adjustment and/or correction, in particular a real-time adjustment and/or a real-time correction of the raw irradiation plan. This is based on the consideration that the raw irradiation plan does not take into account the respiratory phases or deviations in the respiration of the patient during the irradiation, e.g. deeper or shallower, such that if the patient's breathing deviates from the normal respiration, in particular in the case of a deeper or shallower respiration of the patient, this can potentially lead to the unintended irradiation of surrounding healthy tissue. By taking into account the irradiation respiration profile, which in particular reflects the current respiration, the irradiation plan can be determined such that the raw irradiation plan can be adapted in real time to the current respiration and/or respiratory phase. For example, if a deviation of the respiration from the normal respiration is observed during the determination of the irradiation plan based on the irradiation respiration profile, a suspension of the irradiation, a reduction of the dose to be applied and/or greater safety margins can be specified in the irradiation plan for this time period.

In a further method step, the determined irradiation plan is provided, in particular provided to a device intended for irradiation of the patient. In particular, the determined irradiation plan is provided instantaneously or in real time such that the provided irradiation plan can be applied directly for the irradiation. This permits an immediate response to be made to deviations in the respiration of the patient and thus enables an optimized irradiation of the patient.

One or more example embodiments of the present invention are based on the consideration of developing a treatment workflow which takes into account the characteristic features of the acquisition and reconstruction of a respiration-correlated, time-resolved 3D image dataset (e.g. 4DCT data) also in the planning and execution of the irradiation. In order to determine the time-resolved 3D image dataset, a representative respiratory cycle of the patient is calculated. This is used during the data acquisition in order to define when a complete respiratory cycle has been captured and in order to exclude overly shallow, deep or lengthy respiratory cycles. Furthermore, the representative respiratory cycle is used during the determination of the time-resolved 3D image dataset in order to determine the average respiratory cycle length and the characteristic relationship between the respiratory phases and the representative respiratory cycle. This is used during the reconstruction in order to compensate for uncertainties in the respiratory rate or the form of the respiratory cycle.

One or more example embodiments of the present invention are based in particular on the consideration of using the same representative respiratory cycle with uncertainty information (i.e. the same algorithmics) also during the irradiation planning (e.g. taking into account the respiratory variability as uncertainty in robust plan optimization) and for the active control of the irradiation (e.g. gating). In simple terms, the same algorithmics are used for the imaging and the therapy (irradiation) and consequently the beam time for the CT scanner or accelerator is controlled in a consistent manner. By using the same concepts and ideally the identical algorithmics it can be ensured that during the irradiation the anatomy of the patient is the best possible fit to the anatomy that was the basis for the previously calculated irradiation plan.

Optionally, the method comprises determining, in particular calculating, the time-resolved 3D image dataset. The time-resolved 3D image dataset is preferably determined separately from and/or prior to the determination, provision and/or execution of the irradiation plan. In particular, the time-resolved 3D image dataset is determined separated in space and/or time from the determination, provision and/or execution of the irradiation plan. In order to determine the time-resolved 3D image dataset, slice images are taken of the examination region of the patient. The slice images are acquired for example by an imaging apparatus, in particular a computed tomography system, a magnetic resonance tomography system or a positron-emission tomography system. The slice images form in particular a slice image sequence. For a z-position (position along a patient tunnel), the slice image sequence preferably comprises a plurality of slice images acquired spaced apart in time. Furthermore, the slice images can form a stack comprising slice images along the z-direction. The slice images are preferably acquired over a measurement duration of at least 1 minute, in particular at least 3 minutes and more particularly at least 5 minutes. Preferably, each of the slice images includes a timestamp, the timestamp preferably indicating the point in time of the acquisition of the respective slice image. The slice images, in particular the slice image sequence, is provided for further use, in particular for determining the 3D image dataset.

In order to determine the 3D image dataset based on the slice images, the first surrogate variable is determined, defined and/or measured. The first surrogate variable is determined, measured and/or acquired in particular during the acquisition of the slice images. Preferably, the measured, acquired and/or determined first surrogate variable forms a first surrogate variable signal, the first surrogate variable signal and/or the first surrogate variable having a time characteristic and/or a variation with respect to time. For example, measurement points are determined during the definition, determination and/or acquisition of the first surrogate variable, the measurement points describing the value of the first surrogate variable at a respective measurement time point. The measurement point comprises in particular information in respect of the measurement time points. The acquired, determined and/or measured first surrogate variable describes the patient's breathing and/or is correlated with the respiration of the patient during the acquisition of the slice images. Preferably, the timestamps of the slice images and the measurement time points of the measurement of the first surrogate variable are synchronized and/or specified with respect to a reference time. This enables each of the slice images to be assigned a value of the first surrogate variable.

In order to determine the time-resolved 3D image dataset, the imaging respiration profile is defined, determined and/or calculated based on the defined, determined and/or measured first surrogate variable, in particular the first surrogate signal. For example, a computer-implemented algorithm and/or a machine learning method are/is employed to determine the imaging respiration profile. For example, a respiratory curve and/or a temporal description of the respiration, the respiratory cycle and/or the respiratory phases are/is defined, determined and/or calculated as the imaging respiration profile. The time-resolved 3D image dataset is subsequently determined based on the defined, determined, and/or calculated imaging respiration profile. Machine learning methods and/or a computer-implemented algorithm can be employed for this purpose. This enables the respiration of the patient during the acquisition of the slice images to be taken into account in the determination of the 3D image dataset. For example, the time-resolved 3D image dataset can be determined based on slice images of representative and/or normal respiration, and in particular slice images exhibiting too deep or too shallow breathing can be excluded.

Particularly preferably, the first surrogate variable corresponds to the second surrogate variable. In other words, the same physical or sensory quantity is acquired, determined and/or measured as the first and second surrogate variable. For example, the expansion of the rib cage, a volume flow of the respiratory air and/or a movement of a reference point on the body of the patient is acquired, determined and/or measured as the first and/or second surrogate variable. Preferably, the first and the second surrogate variable are acquired, determined and/or measured based on the same measurement method and/or the same sensor type.

In a possible embodiment of the method it is provided that the imaging respiration profile comprises a plurality of respiratory phases. The imaging respiration profile and/or the irradiation respiration profile can comprise a normal respiratory phase, a deep respiratory phase, a shallow respiratory phase and/or a deviation respiratory phase as respiratory phases. The time-resolved 3D image dataset is preferably acquired and/or determined based on the normal respiratory phase and/or normal respiratory phases. In other words, the time-resolved 3D image dataset preferably describes a time-resolved 3D image dataset and/or slice image sequence for a normal respiratory phase. For example, slice images that were acquired during a deep respiratory phase, a shallow respiratory phase and/or a deviation respiratory phase are excluded and/or not taken into account in the determination of the time-resolved 3D image dataset. The raw irradiation plan forms and/or is determined as an irradiation plan for normal respiratory phases of the patient. During the determination of the irradiation plan, in particular during the real-time adjustment of the irradiation plan, or of the raw irradiation plan, the irradiation respiration profile can be examined for normal respiratory phases, deep respiratory phases, shallow respiratory phases and/or deviation respiratory phases, the raw irradiation plan being determined, set and/or provided as the irradiation plan for normal respiratory phases, the raw irradiation plan being omitted, modified and/or suspended as the irradiation plan for deep respiratory phases, shallow respiratory phases and/or deviation respiratory phases, or respiratory phases different from the normal respiratory phase.

An embodiment of the method, according to the present invention, provides that an organ movement is determined based on the 3D image dataset and the imaging respiration profile, alternatively and/or in addition based on the 3D image dataset and the irradiation respiration profile. For example, the movement of the organ to which the target volume belongs may be understood as an organ movement. In particular, the organ movement can describe a movement of the target volume. The organ movement is based on or results from the respiration of the patient such that the organ movement is in particular correlated with the respiration of the patient, the irradiation respiration profile and/or the imaging respiration profile. The organ movement can be formed as a movement relative to the environment, for example another organ or a bone skeleton. Alternatively and/or in addition, the organ movement can be determined as an absolute movement, in particular relative to a global coordinate system. In this case it can be provided that the irradiation plan is determined based on the organ movement. For example, the raw irradiation plan is adapted and/or corrected based on the organ movement. This embodiment is based on the consideration that the organ movement induced by the respiration can be determined based on the irradiation respiration profile and/or the imaging respiration profile such that it is possible to localize on a movement of an organ, in particular of the target volume, as a function of the respiration and consequently the irradiation plan can be determined and/or adjusted in real time.

It is particularly preferred that the irradiation plan and/or the raw irradiation plan for the target volume comprises or defines a safety zone, also referred to as a safety margin. The safety zone is a region, preferably a volume, which is arranged around the target volume and defines an area which for safety reasons is excluded from the irradiation so that intact tissue and/or healthy organs are not damaged unintentionally. The safety zone can be provided in order to be able to respond to movements of the target volume, of the organ or movements of the patient. For example, an embodiment of the method, according to the present invention, provides that the safety zone is defined, determined and/or adjusted based on the 3D image dataset, the imaging respiration profile and/or the irradiation respiration profile. For example, it can be provided that the safety zone is chosen smaller for normal respiratory phases than for deep respiratory phases, shallow respiratory phases or deviation respiratory phases. This embodiment results in particular from the need to avoid interrupting irradiation processes during respiratory phases that do not form a normal respiratory phase, which is made possible by the adjustment of the safety zones.

In particular it is provided that the irradiation plan comprises irradiation variables, the irradiation variables being determined and/or specified in particular during the determination of the irradiation plan. In order to determine the irradiation plan, for example, the irradiation variables of the raw irradiation plan are adjusted based on the 3D image dataset, the irradiation respiration profile and/or the imaging respiration profile. As irradiation variables, the irradiation plan comprises for example a beam diameter, a focus position of a beam intended for irradiation, a dose rate of the beam, a pulsing of the beam and/or a receiving point of the beam on the patient.

An embodiment of the present invention provides that the 3D image dataset is determined via a first algorithm based on the acquired slice images and the irradiation respiration profile. The first algorithm is embodied to take into account the respiration during the acquisition of the slice images, in particular the imaging respiration profile, in the determination of the 3D image dataset. The irradiation plan is determined based on the 3D image dataset and the irradiation respiration profile preferably via a second algorithm. The second algorithm is embodied and/or configured to determine the irradiation plan based on the imaging respiration profile and/or to adapt the raw irradiation plan. In particular, the second algorithm is embodied to determine the imaging respiration profile based on the second surrogate variable. Preferably, the first algorithm and the second algorithm are based on a similar or the same utilization of a surrogate variable. In particular, the first algorithm and the second algorithm are embodied and/or configured for the same or similar processing of the surrogate signal in order to form a respiration profile. In particular, the second algorithm is or was obtained from the first algorithm by transfer learning.

It is particularly preferred that the 3D image dataset is determined based on the slice images and the imaging respiration profile via machine learning. In particular, it can also be provided that the imaging respiration profile is determined based on the first surrogate variable via machine learning. It can further be provided that the irradiation respiration profile is determined and/or calculated based on the second surrogate variable and/or the irradiation plan is determined and/or acquired based on the 3D image dataset and the irradiation respiration profile via machine learning. The machine learning can be implemented via a trained function, the first and/or the second algorithm for example forming a trained function and/or a machine learning algorithm.

A further subject matter of one or more example embodiments of the present invention is formed by a device for determining the irradiation plan. The device can be for example a computer device, for example in the form of a personal computer or a cloud device. It is particularly preferred that the device is an irradiation device or part of an irradiation device. The device comprises a first and a second acquisition unit, a first and a second determination unit and a provisioning unit, the first acquisition unit being embodied to acquire the time-resolved 3D image dataset, the 3D image dataset being time-resolved over at least one respiratory cycle of the patient, the 3D image dataset being based on a time-resolved scan of an examination region of a patient and on an imaging respiration profile, the examination region comprising the target volume, the imaging respiration profile being based on a first respiration-correlated surrogate variable determined during the time-resolved scan. The second acquisition unit is embodied to acquire the respiration-correlated second surrogate variable of the patient, the second surrogate variable describing a respiration of the patient during the irradiation. The first determination unit is embodied to determine the irradiation respiration profile based on the acquired second surrogate variable. The second determination unit is embodied to determine the irradiation plan based on the time-resolved 3D image dataset and the irradiation respiration profile. The provisioning unit is embodied to provide the irradiation plan for an irradiation of the target volume.

A further subject matter of one or more example embodiments of the present invention is formed by a device for applying and/or executing the irradiation plan. The device forms in particular an irradiation device. For example, the device, in particular the irradiation device, comprises and/or forms a linear accelerator for irradiating a patient. In particular, the device for applying and/or executing the irradiation plan comprises an irradiation source which is embodied to emit a beam of ionizing radiation and/or a beam formed from particles (particle beam) for irradiating the target volume. The device for applying and/or executing the irradiation plan comprises an application unit, the application unit being embodied to execute and/or apply the irradiation plan, provided for example by the device for determining the irradiation plan, for example to actuate the radiation source in order to emit the beam in accordance with the irradiation plan.

A further subject matter of one or more example embodiments of the present invention is formed by a computer program product. The computer program product comprises and/or forms a computer program which can be loaded directly into a computing device. The computer program product has program sections. The computer program product, in particular the computer program and/or the program sections, is embodied to perform the steps of the inventive method for providing the irradiation plan when the computer program is executed in the computing device or the device for providing the irradiation plan.

One or more example embodiments of the present invention further relate to a computer-readable medium, for example a DVD, CD, USB memory or cloud storage. The computer program and/or the computer program product according to the invention are/is stored on the medium.

BRIEF DESCRIPTION OF THE DRAWINGS

Further advantages, effects and embodiments will become apparent from the attached figures and the description thereof. In the figures.

DETAILED DESCRIPTION

Figure 1:
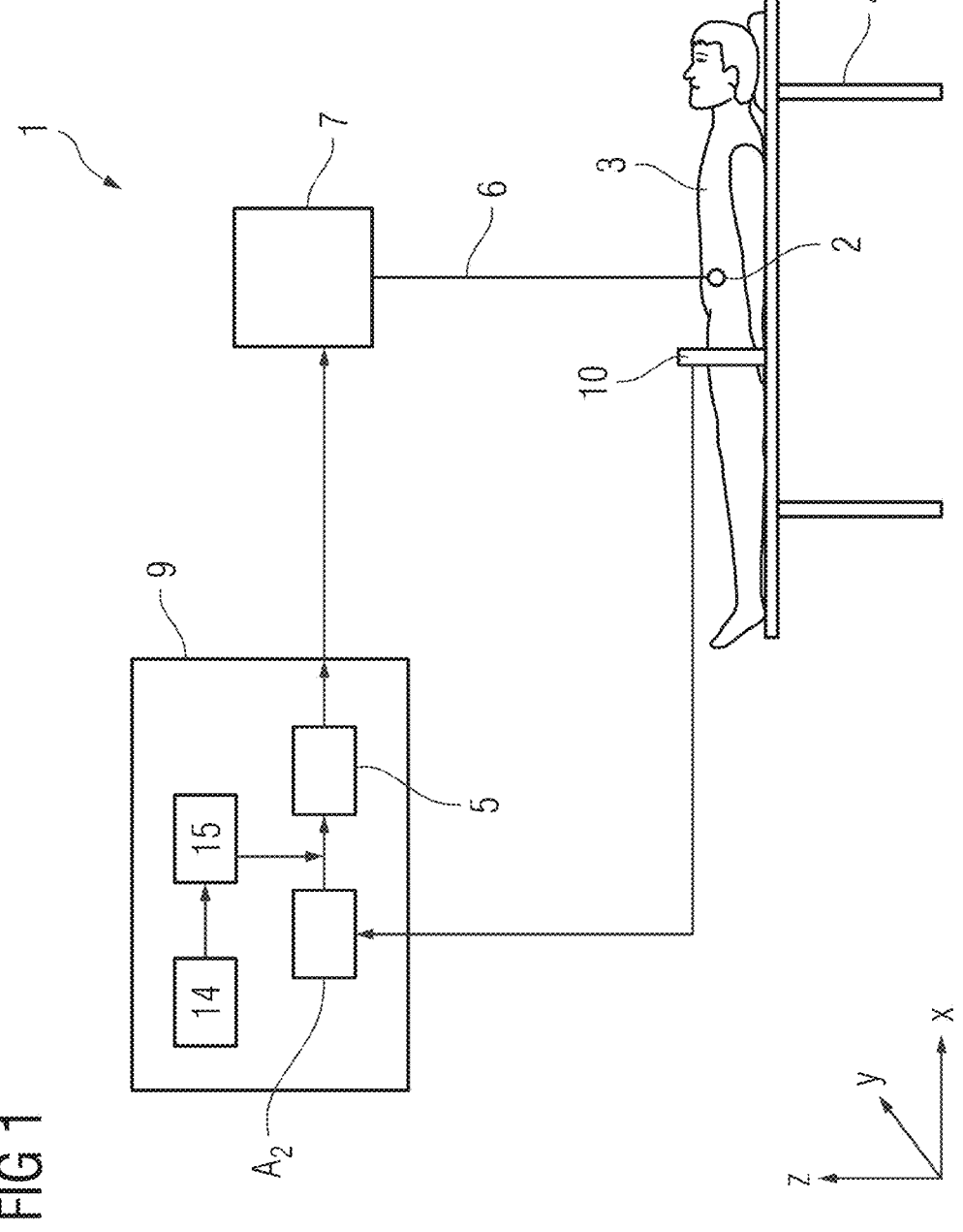
FIG. 1 schematically shows an exemplary embodiment of a device for irradiating a target volume, FIG. 2 schematically shows a movement of the target volume in a patient.

The device 1 schematically illustrated in FIG. 1 for irradiating a target volume 2, in particular a patient 3 comprising the target volume 2, forms a linear accelerator, for example. For supporting and positioning the patient 3 during the irradiation, the device 1 comprises a positioning device 4 (e.g. a table). During the irradiation, the positioning device 4 and the patient 3 are located in an irradiation room. The patient 3, or the target volume 2, is irradiated by the device 1 with a beam 6 of ionizing radiation (photons or particles such as protons, helium) based on an irradiation plan 5. By such a beam 6, a tumor, for example, can be irradiated with high-energy radiation as the target volume 2.

The irradiation via the beam 6 is performed from a fixed direction such that the patient 3 to be irradiated is arranged beforehand fixed in space in the irradiation room by the positioning device 4. Alternatively, an irradiation of the patient 3 from different directions can be provided, for example by use of a gantry 7, in particular a rotatable gantry, which is arranged to be movable around an axis. The beam 6 is directed onto the body to be irradiated or the target volume 2 with the aid of a beamline of the gantry 7.

Figure 2:
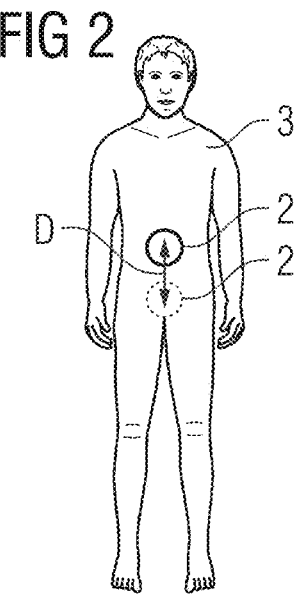

The target volume 2 comprises or is formed by a tumor, for example. The target volume 2 is for example part of an organ, e.g. of the lung, the kidneys or the stomach. The target volume 2 is subject to a movement, e.g. relative to the bone skeleton or the positioning device 4. This movement of the target volume 2 is based on the respiration of the patient 3, in particular on the movement of the diaphragm and/or the expansion and contraction of the rib cage. The target volume 2 can be assigned a zero position, or reference position, which corresponds for example to the orientation and/or position of the target volume 2 at a point in time between inspiration and expiration. The inspiration and expiration, or the movement of the target volume 2, leads to the target volume 2 moving away from the zero position or the reference position during a respiratory cycle. This movement of the target volume 2 and/or the deviation of the orientation or position of the target volume 2 from the zero position or reference position is dependent on the respiration and consequently is correlated with an irradiation respiration profile A2 and in particular with a second respiration-correlated surrogate variable S2. The movement of the target volume 2 is shown in FIG. 2.

The target volume 2 can be specified or described in its position in its orientation via x and y coordinates in an x-y plane, which is given for example by a bearing surface of the patient couch or positioning device 4. For targeted irradiation of the target volume 2 in the x-y plane, the patient 3 can be positioned or moved via the positioning device 4 or the gantry 7 can be positioned or moved relative to the patient 3. A z-position of the target volume 2 can be described viaz coordinates, the z-axis standing perpendicular to the x-y plane. The target volume 2 can be described in particular via a set of raster points P(x, y, z) that lie within the target volume 2. For targeted radiation deposition in the z-direction, the patient 3 can be moved vertically via the positioning device 5, the gantry 7 varied in the z-direction or beam parameters of the beam 6 adjusted. Examples of beam parameters are a beam energy, a particle energy, a beam diameter, a beam divergence, a beam focus, a pulsing and/or an energy distribution. The beam parameters and/or the receiving point of the beam 6 during the irradiation are determined based on the position of the target volume 2 and taking into account the irradiated body, e.g. via a CT scan and/or a time-resolved 3D image dataset 8. The beam parameters form in particular a part of the irradiation plan 5.

According to one or more example embodiments of the present invention, the irradiation plan 5 is determined based on the irradiation respiration profile A2. The irradiation device 1 preferably comprises a device 9 for determining the irradiation plan 5. In order to perform the actual irradiation, the irradiation plan 5 is forwarded from the device 1 to a beam generation device and a controller for its execution.

The device 1 comprises a measurement unit 10, for example a respiration belt for detecting a respiration of the patient 3 while he or she is disposed on the positioning device 4 and/or is being irradiated. Alternatively, the measurement unit 10 can be formed by a camera which optically captures the respiration of the patient 3. The respiration acquired by the measurement unit 10 is referred to as the second surrogate variable S2 and is provided for further use. For this purpose, the measurement unit is connected to the device 9 via the data communications connection 11. In order to determine the irradiation plan 5, the device 9 or the method for determining the irradiation plan 5 is provided with input data, the input data comprising the position and the dimensions of the target volume 2 to be irradiated (e.g. of a tumor that is to be irradiated), the condition of the tissue that is irradiated by the beam 6 on the way to the target volume 2 and a predetermined dose distribution (nominal dose distribution).

FIG. 2 schematically shows a patient 3 in order to illustrate a respiration-correlated movement of a target volume 2. The patient has an internal organ, e.g. a liver, as the target volume 2. The internal organ and hence the target volume 2 moves due to a respiratory movement of the patient P. The target volume 2 is illustrated for two different respiratory phases, once with continuous lines and once with dashed lines. It can be seen from FIG. 2 that the target volume 2 moves between these two respiratory phases in the movement direction D.

Figure 3:
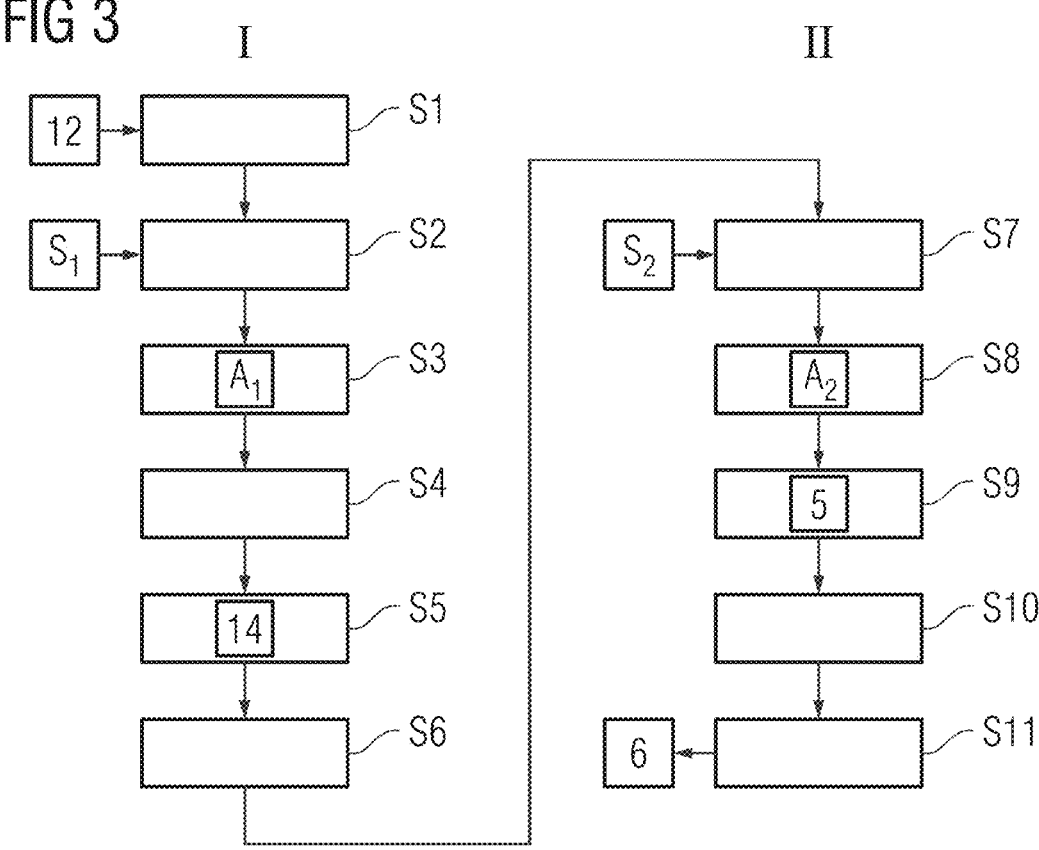
FIG. 3 shows a schematic flowchart for a method for providing an irradiation plan.

FIG. 3 shows a flowchart of an embodiment of the inventive method for providing an irradiation plan 5. The flowchart is divided into two sections I and II, where section I shows the method part for providing and/or determining the time-resolved 3D image dataset and section II shows the part of the method which is embodied for determining the irradiation plan 5 based on the 3D image dataset.

In step S1, raw image data 12 is acquired from an examination volume of a patient 3. The raw image data 12 is also referred to as slice images and/or forms such. During the operation of a computed tomography system, an X-ray source sends X-ray beams in the direction of an X-ray detector, the X-ray beams passing through the patient 3 and being recorded by the X-ray detector in the form of measurement signals. During the scan, the combination of X-ray source assembly and X-ray detector moves along a spiral path around the z-axis of the CT system and captures the measurement signals from all radial directions.

In step S2, a first surrogate variable S1 is measured which describes a respiration of the patient 3. For example, the first surrogate variable S1 is measured via a respiration belt. The first surrogate variable S1 is measured during the acquisition of the raw image data 12.

In step S3, an imaging respiration profile A1 is determined based on the first surrogate variable S1, for example as a respiratory curve. The imaging respiration profile A1 describes the respiratory movement of the patient 3 over at least one respiratory cycle.

In step S4, which is optional, at least one measurement parameter of the computed tomography system, or of the device for acquiring the raw image data, is derived based on the provided imaging respiration profile A1 via a computing unit, the derived measurement parameter determining for example a temporal resolution of a set of slice images of the raw image data 12.

In step S5, the time-resolved 3D image dataset 14 is determined based on the raw image data 12 and the imaging respiration profile A1. For example, the device for acquiring the raw image data 12, in this case the computed tomography system, is actuated via a control unit for the purpose of generating and/or determining the time-resolved 3D image dataset 14 based on the automatically derived measurement parameter, during which process a plurality of projection datasets are acquired from different projection angles for the at least one z-position in the course of a relative rotational movement between a radiation source of the computed tomography system and the patient 3 and the at least one 3D image dataset 14 is generated based thereon. The 3D image dataset 14 may comprise the associated imaging respiration profile A1, for example as metadata.

In method step S6, the time-resolved 3D image dataset from step S5 is provided. For example, the irradiation plan is forwarded by a data communications connection between the irradiation device 1 and the computed tomography system. In particular, the imaging respiration profile A1 is provided in addition to the irradiation plan 5 or included in the irradiation plan 5. The data is provided in particular to the irradiation device 1 and/or the device 9 for determining the irradiation plan 5.

In step S7, a second surrogate variable S2 is determined, in particular measured. The second surrogate variable S2 is a correlated quantity in respect of the respiration of the patient 3 and is measured for example via a respiration belt or a video recording of the rib cage of the patient 3. The second surrogate variable S2 is measured while the patient 3 is positioned for the irradiation, in particular during the execution of the irradiation.

Figure 4:
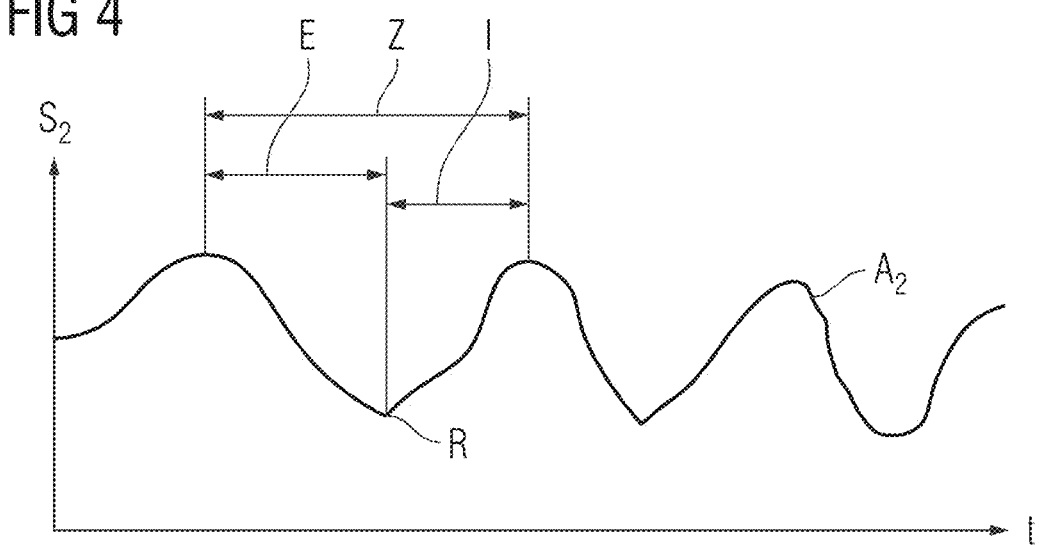
FIG. 4 shows an example of an irradiation respiration profile, and FIG. 5 schematically shows an interaction between imaging respiration profile and irradiation respiration profile.

In step S8, an irradiation respiration profile A2 of the patient 3 is determined based on the second surrogate variable S2. The irradiation respiration profile A2 is determined for example as a respiratory curve which describes the variation with time of the respiration or of the respiratory phases. An example irradiation respiration profile A2 is shown in FIG. 4.

In step S9, the irradiation plan 5 is determined based on the irradiation respiration profile A2 and the time-resolved 3D image dataset 14. For example, a raw irradiation plan based on the irradiation respiration profile A2, the 3D image dataset 14 and in particular the imaging respiration profile A1 is adapted and/or corrected in real time for this purpose. For example, the irradiation can be discontinued or varied for respiratory phases in the irradiation respiration profile A2 that deviate from a normal respiration and/or a respiration during the imaging.

The determined irradiation plan 5, in particular in the form of a real-time correction of the raw irradiation plan, is provided in method step S10, for example to the irradiation device 9.

In a step S11, the determined irradiation plan 5 is applied or executed by the irradiation device 9. It can be provided for example that the raw irradiation plan is stored and executed in the irradiation device 9, the real-time corrected irradiation plan 5 being determined for respiratory phases in the irradiation plan 5 that deviate from a normal respiration, and being executed for a defined or definable time instead of the raw irradiation plan 5. The time of the execution corresponds for example to the duration of a respiratory phase or a respiratory cycle.

FIG. 4 shows by way of example an irradiation respiration profile A2 of a patient 3. The irradiation respiration profile A2 describes the respiration of the patient 3 over time z. The depicted irradiation respiration profile A2 extends over several respiratory cycles Z. Each respiratory cycle Z has an exhalation phase E and an inhalation phase I. Furthermore, the irradiation respiration profile comprises rest phases R between a respective exhalation and an inhalation, a respiratory movement being barely visible in the rest phases R.

Figure 5:
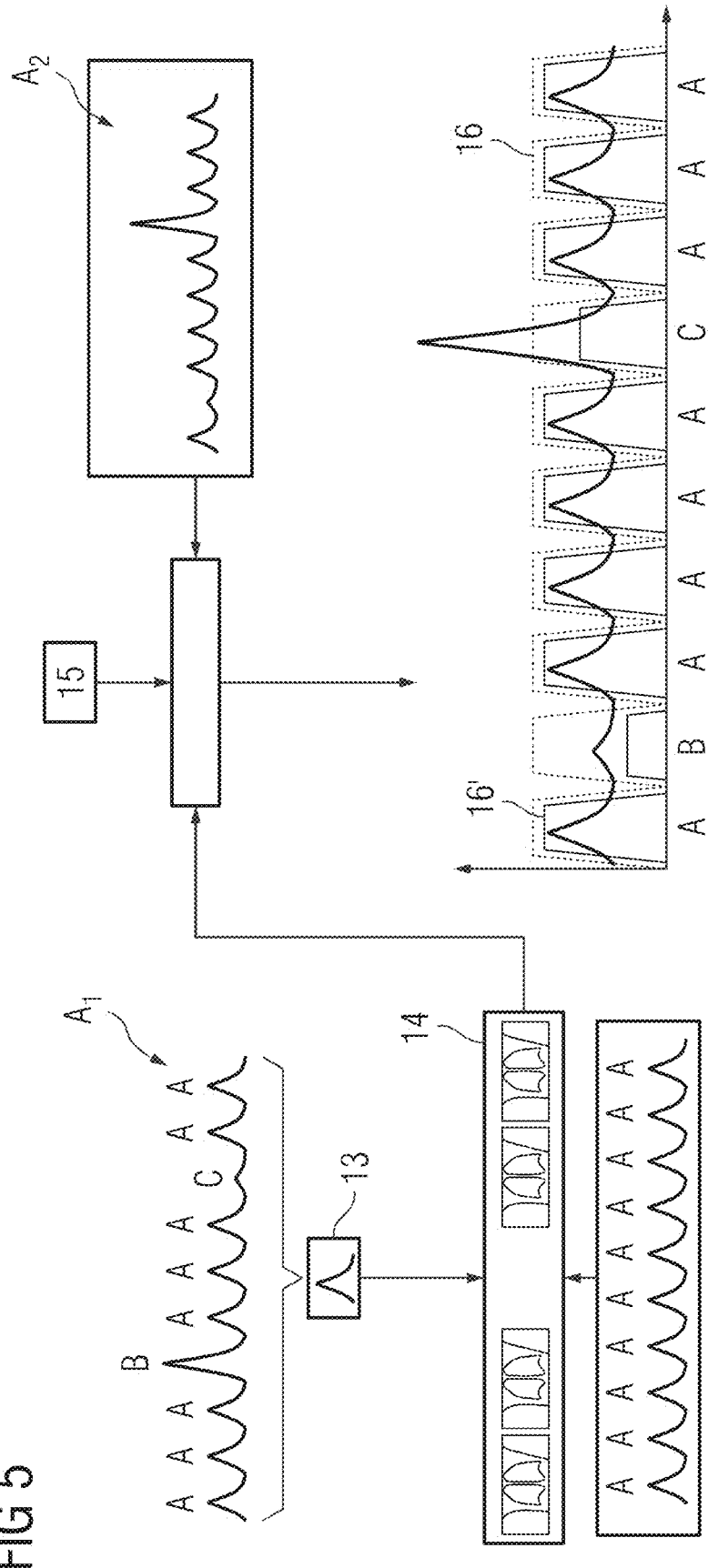

FIG. 5 once again illustrates the relationship between imaging respiration profile A1, irradiation respiration profile A2 and irradiation plan 5. During the acquisition of the raw image data 12, the imaging respiration profile A1 was determined for a patient 3, said imaging respiration profile comprising the cycle A multiple times as normal respiration, once the cycle B (e.g. very deep breathing) and once the cycle C (shallow breathing). The 3D image dataset 14 was determined based on the imaging respiration profile A1. The 3D image dataset 14 was determined in particular based on a representative respiratory cycle 13, which in this case corresponds to the cycle A of the normal respiration. If the patient 3 breathes during the irradiation according to the irradiation respiration profile A2 (ACAAAABAAA), an irradiation according to the raw irradiation plan 15 is not optimal, at least for the phases B and C, because the irradiation based on the irradiation plan 15 assumes representative respiratory cycles 13. In other words, the raw irradiation plan 15 is based on a respiration comprising the cycles AAAA. Consequently, in the course of an irradiation using the raw irradiation plan 15, the irradiation dose would be applied suboptimally during the respiratory cycle B and the respiratory cycle C.

The method according to one or more example embodiments of the present invention therefore provides that the raw irradiation plan 15 is adapted based on the irradiation respiration profile A2 and in particular on the 3D image dataset 14 and in this way the irradiation plan 5 is determined. Whereas the raw irradiation plan 15 resulting from an AAAA respiration provides the depicted pulsing 16 of the beam 6, which pulsing is the same for each respiratory cycle with the same radiation pulses (e.g. same pulse length, beam power), the irradiation plan 5 determined taking into account the irradiation respiration profile A2, comprises different pulses in the pulsing 16', in particular the beam 6 has different beam parameters (beam power, pulse length) for the cycles B and C than for the cycles A.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

We claim:

1. A method for providing an irradiation plan for irradiation of a target volume, the method comprising:
acquiring a time-resolved 3D image dataset, wherein the time-resolved 3D image dataset is time-resolved over at least one respiratory cycle of a patient, wherein the time-resolved 3D image dataset is based on time-resolved computed tomography (CT) scans of an examination region of the patient and based on an imaging respiration profile, wherein the examination region includes the target volume, and wherein the imaging respiration profile is based on a respiration-correlated first surrogate variable determined during the time-resolved CT scans;
measuring a respiration-correlated second surrogate variable of the patient during execution of the irradiation plan, wherein the respiration-correlated second surrogate variable describes a respiration of the patient during irradiation;
determining an irradiation respiration profile based on the respiration-correlated second surrogate variable;
adjusting the irradiation plan based on the time-resolved 3D image dataset and the irradiation respiration profile; and
providing the irradiation plan for irradiation of the target volume.

2. The method as claimed in claim 1, further comprising:
determining, prior to the acquiring of the time-resolved 3D image dataset, the time-resolved 3D image dataset, wherein the determining of the time-resolved 3D image dataset includes
acquiring slice images of the examination region via an imaging apparatus and providing the slice images,
acquiring the respiration-correlated first surrogate variable, wherein the respiration-correlated first surrogate variable describes a respiration of the patient during the acquiring of the slice images,
determining the imaging respiration profile based on the respiration-correlated first surrogate variable, and
determining the time-resolved 3D image dataset based on the slice images and the imaging respiration profile.

3. The method as claimed in claim 2, wherein the respiration-correlated second surrogate variable corresponds to the respiration-correlated first surrogate variable.

4. The method as claimed in claim 1,
wherein the imaging respiration profile includes respiratory phases,
wherein the respiratory phases include at least one of a normal respiratory phase or a deep respiratory phase, and at least one of a shallow respiratory phase or a deviation respiratory phase,
wherein the time-resolved 3D image dataset is determined based on at least one of the normal respiratory phase or the deep respiratory phase, while at least one of the shallow respiratory phase or the deviation respiratory phase are excluded during determination of the time-resolved 3D image dataset,
wherein the irradiation respiration profile is examined for at least one of the normal respiratory phase, the deep respiratory phase, the shallow respiratory phase or the deviation respiratory phase, and
wherein the irradiation plan is determined such that an irradiation of the target volume is at least one of different from irradiation for the normal respiratory phase or omitted for at least one of the deep respiratory phase, the shallow respiratory phase or the deviation respiratory phase.

5. The method as claimed in claim 1, wherein at least one of an organ movement or a movement of the target volume is determined based on at least one of the time-resolved 3D image dataset, the imaging respiration profile or the irradiation respiration profile, and wherein the adjusting the irradiation plan adjusts the irradiation plan based on at least one of the organ movement or the movement of the target volume.

6. The method as claimed in claim 1, wherein the irradiation plan for the target volume includes a safety zone, wherein the safety zone is determined based on at least one of the time-resolved 3D image dataset, the imaging respiration profile or the irradiation respiration profile.

7. The method as claimed in claim 1, wherein the irradiation plan includes irradiation parameters, wherein at least one of a beam diameter, a focus position of a beam intended for the irradiation, a dose rate of the beam, a pulsing of the beam, or a receiving point of the beam on the patient, are determined as the irradiation parameters during the adjusting of the irradiation plan based on the time-resolved 3D image dataset and the irradiation respiration profile.

8. The method as claimed in claim 1, wherein the time-resolved 3D image dataset was or is determined based on an analysis of the imaging respiration profile via a first analysis algorithm, and wherein the adjusting the irradiation plan adjusts the irradiation plan based on an analysis of the irradiation respiration profile via the first analysis algorithm.

9. The method as claimed in claim 1, wherein at least one of determination of the imaging respiration profile or determination of the time-resolved 3D image dataset was or is determined based on a first machine-learning algorithm, wherein a further machine-learning algorithm is applied to at least one of determine the irradiation respiration profile or determine the irradiation plan, wherein the further machine-learning algorithm is or was obtained based on a transfer learning of the first machine-learning algorithm.

10. A device for determining an irradiation plan for irradiation of a target volume, the device comprising:
a first acquisition unit configured to acquire a time-resolved 3D image dataset, wherein the time-resolved 3D image dataset is time-resolved over at least one respiratory cycle of a patient, wherein the time-resolved 3D image dataset is based on time resolved computed tomography (CT) scans of an examination region of the patient and based on an imaging respiration profile, wherein the examination region includes the target volume, wherein the imaging respiration profile is based on a respiration-correlated first surrogate variable determined during the time-resolved CT scans;

a second acquisition unit configured to measure a respiration-correlated second surrogate variable of the patient during execution of the irradiation plan, wherein the respiration-correlated second surrogate variable describes a respiration of the patient during irradiation;

a first determination unit configured to determine an irradiation respiration profile based on the respiration-correlated second surrogate variable;

a second determination unit configured to adjust the irradiation plan based on the time-resolved 3D image dataset and the irradiation respiration profile; and a provisioning unit configured to provide the irradiation plan for irradiation of the target volume.

11. The device as claimed in claim 10, further comprising:

an irradiation source configured to emit a beam of ionizing radiation to irradiate the target volume; and an application unit configured to at least one of actuate or control the irradiation source to output the beam based on the irradiation plan.

12. The device as claimed in claim 11, further comprising:

a measurement unit configured to measure the respiration-correlated second surrogate variable during irradiation of the target volume.

13. A non-transitory computer program product including a computer program loadable into a computing device, the computer program having program sections that, when executed at the computing device, cause the computing device to perform the method as claimed in claim 1.

14. A non-transitory computer-readable medium storing program sections that, when executed by a computing device, cause the computing device to perform the method as claimed in claim 1.

15. A device for determining an irradiation plan for irradiation of a target volume, the device comprising:

a memory storing computer-readable instructions; and at least one processor configured to execute the computer-readable instructions to cause the device to acquire a time-resolved 3D image dataset, wherein the time-resolved 3D image dataset is time-resolved over at least one respiratory cycle of a patient, wherein the time-resolved 3D image dataset is based on time-resolved computed tomography (CT) scans of an examination region of the patient and based on an imaging respiration profile, wherein the examination region includes the target volume, and wherein the imaging respiration profile is based on a respiration-correlated first surrogate variable determined during the time-resolved CT scans, measure a respiration-correlated second surrogate variable of the patient during execution of the irradiation plan, wherein the respiration-correlated second surrogate variable describes a respiration of the patient during irradiation, determine an irradiation respiration profile based on the respiration-correlated second surrogate variable, adjust the irradiation plan based on the time-resolved 3D image dataset and the irradiation respiration profile, and provide the irradiation plan for irradiation of the target volume.

16. The method as claimed in claim 2, wherein the imaging respiration profile includes respiratory phases, wherein the respiratory phases include at least one of a normal respiratory phase, a deep respiratory phase, a shallow respiratory phase or a deviation respiratory phase, wherein the time-resolved 3D image dataset is determined based on at least one of the normal respiratory phase or the deep respiratory phase, while at least one of the shallow respiratory phase or the deviation respiratory phase are excluded during determination of the time-resolved 3D image dataset, wherein the irradiation respiration profile is examined for at least one of the normal respiratory phase, the deep respiratory phase, the shallow respiratory phase or the deviation respiratory phase, and wherein the adjusting the irradiation plan adjusts the irradiation plan such that an irradiation of the target volume is at least one of different from irradiation for the normal respiratory phase or omitted for at least one of the deep respiratory phase, the shallow respiratory phase or the deviation respiratory phase.

17. The method as claimed in claim 3, wherein the imaging respiration profile includes respiratory phases, wherein the respiratory phases include at least one of a normal respiratory phase, a deep respiratory phase, a shallow respiratory phase or a deviation respiratory phase, wherein the time-resolved 3D image dataset is determined based on at least one of the normal respiratory phase or the deep respiratory phase, while at least one of the shallow respiratory phase or the deviation respiratory phase are excluded during determination of the time-resolved 3D image dataset, wherein the irradiation respiration profile is examined for at least one of the normal respiratory phase, the deep respiratory phase, the shallow respiratory phase or the deviation respiratory phase, and wherein the adjusting the irradiation plan adjusts the irradiation plan such that an irradiation of the target volume is at least one of different from irradiation for the normal respiratory phase or omitted for at least one of the deep respiratory phase, the shallow respiratory phase or the deviation respiratory phase.

18. The method as claimed in claim 4, wherein at least one of an organ movement or a movement of the target volume is determined based on at least one of the time-resolved 3D image dataset, the imaging respiration profile or the irradiation respiration profile, and wherein the adjusting the irradiation plan adjusts the irradiation plan based on at least one of the organ movement or the movement of the target volume.

19. The method as claimed in claim 2, wherein at least one of determination of the imaging respiration profile or determination of the time-resolved 3D image dataset was or is determined based on a first machine-learning algorithm, wherein a further machine-learning algorithm is applied to at least one of determine the irradiation respiration profile or determine the irradiation plan, wherein the further machine-learning algorithm is or was obtained based on a transfer learning of the first machine-learning algorithm.

20. The method as claimed in claim 4, wherein at least one of determination of the imaging respiration profile or determination of the time-resolved 3D image dataset was or is determined based on a first machine-learning algorithm, wherein a further machine-learning algorithm is applied to at least one of determine the irradiation respiration profile or determine the irradiation plan, wherein the further machine-learning algorithm is or was obtained based on a transfer learning of the first machine-learning algorithm.

* * * * *